United States Patent [19]

Hiller

[11] 4,235,880

[45] Nov. 25, 1980

[54] ANIMAL FEEDS CONTAINING A MIXTURE OF TYLOSIN AND PROTEOLYTIC ENZYMES

[75] Inventor: Guenter Hiller, Erkrath, Fed. Rep. of Germany

[73] Assignee: Henkel Kommanditgesellschaft auf Aktien, Dusseldorf-Holthausen, Fed. Rep. of Germany

[21] Appl. No.: 61,628

[22] Filed: Jul. 30, 1979

Related U.S. Application Data

[63] Continuation of Ser. No. 917,984, Jun. 22, 1978, abandoned.

[30] Foreign Application Priority Data

Jun. 27, 1977 [DE]  Fed. Rep. of Germany ....... 2728850

[51] Int. Cl.$^3$ .............................................. A61K 37/48
[52] U.S. Cl. ..................................................... 424/94
[58] Field of Search .......................................... 424/94

[56] References Cited

U.S. PATENT DOCUMENTS

2,906,621  9/1959  Catron ................................... 424/94

FOREIGN PATENT DOCUMENTS

46-23622  7/1971  Japan ....................................... 424/94

OTHER PUBLICATIONS

Chem. Abstr. vol. 71 (1969), 20010x; vol. 77 1972, 7088k.

Primary Examiner—Frederick E. Waddell
Attorney, Agent, or Firm—Hammond & Littell, Weissenberger and Muserlian

[57] ABSTRACT

Animal feeds based on carbohydrates, protein, fats, and optionally conventional additives, containing from 5 to 50 ppm of the antibiotic tylosin and a content of proteolytic enzymes in such an amount that the enzymatic activity is from 0.05 to 2.5 mTU/gm of said animal feed.

2 Claims, No Drawings

ANIMAL FEEDS CONTAINING A MIXTURE OF TYLOSIN AND PROTEOLYTIC ENZYMES

This is a continuation of Ser. No. 917,984, filed June 22, 1978, and now abandoned.

BACKGROUND ART

High-potency animal feeds, as they are normally used today in intensive animal raising, contain a number of additives of prophylactic and/or nutritive effect. These include, among others, antibiotics and enzymes. While the use of antibiotics has found acceptance in mixed feeds of all kinds, enzymes are not as yet used on a large scale in the field.

The feed mixtures used in modern intensive animal-raising programs are generally optimized in all nutrient components to such an extent that further improvement does not seem readily possible. However, it is surprising to find that even optimally composed high strength feeds can still be improved with regard to feed utilization and/or the weight increase attainable thereby by adding to these feeds certain antibiotics together with proteolytic enzymes.

OBJECTS OF THE INVENTION

An object of the present invention is the development of a mixture of antibiotics and enzymes which improves the efficiency of animal feeds.

Another object of the invention is the development of a high efficiency animal feed composed of carbohydrates, protein, fats and optionally conventional additives containing from 5 to 50 ppm of the antibiotic tylosin and a content of proteolytic enzymes in such an amount that the enzymatic activity is from 0.05 to 2.5 mTU/gm of said animal feed.

A further object of the invention is the development of a method for efficient rearing of animals comprising feeding animals a high efficiency animal feed based on carbohydrates, protein, fats and optionally conventional additives, containing from 5 to 50 ppm of the antibiotic tylosin and a content of proteolytic enzymes in such an amount that the enzymatic activity is from 0.05 to 2.5 mTU/gm of said animal feed.

These and other objects of the invention will become more apparent as the description thereof proceeds.

DESCRIPTION OF THE INVENTION

It has been surprisingly found that even optimally composed high-potency (high efficiency) feeds can be further improved with respect to feed utilization and/or the weight gain attainable therewith by adding to these feeds certain antibiotics together with proteolytic enzymes.

The subject of the invention accordingly is an animal feed mixture composed of carbohydrates, protein, and fats and optionally the customary additives, having a content of 5 to 50 ppm of the antibiotic tylosin and of proteolytic enzymes in such an amount that an enzymatic activity of 0.05 to 2.5 mTU/gm is present.

More particularly, the present invention relates to a high efficiency animal feed based on carbohydrates, protein, and fats and optionally the customary additives, having a content of 5 to 50 ppm of the antibiotic tylosin and of proteolytic enzymes in such an amount that an enzymatic activity of 0.05 to 2.5 mTU/gm of said animal feed is present; as well as a method for efficient rearing of animals comprising feeding animals a high efficiency animal feed based on carbohydrates, protein and fats and optionally the customary additives, having a content of 5 to 50 ppm of the antibiotic tylosin and of proteolytic enzymes in such an amount that an enzymatic activity of 0.05 to 2.5 mTU/gm of said animal feed is present.

The antibiotic tylosin belongs to the group of the macrolide antibiotics and is obtained in known manner by fermentation of Streptomyces fradiae. The total empirical formula is: $C_{46}H_{77}NO_{17}$.

Suitable proteolytic enzymes to be employed according to the invention are obtained above all by culturing microorganisms and separation of the enzymes produced from the culture solutions. The processes for this are known. Proteolytic enzymes can be used as produced, for example, from Bacillus licheniformis, Bacillus natta, Bacillus subtilis, etc. Especially preferred are acid proteases, e.g., from Aspergillus niger or those described in U.S. Pat. Nos. 3,674,644 and 3,677,898. Acid proteases from the genus Tramates or from Rhizopus rhizopodiformis according to U.S. patent application Ser. No. 695,453, filed June 14, 1976, and now U.S. Pat. No. 4,062,732 are particularly preferred. Such proteases have a particularly wide spectrum of action in the weakly acid range between pH 2.5 and 6.5. These acid proteases preferably have a range of 50% of maximum activity between a pH of 2.5 and a pH of 6.5.

Commercial feed mixtures are optimally composed for the special needs of the various animal species. They are customarily based on carbohydrates, proteins and fats with optional customary feed supplements or additives. The carbohydrates are chiefly from cereal components, corn or the like. The protein carriers are primarily extracted soybean meal pellets, fish meal, animal body meal, bran and the like. Essential amino acids which are lacking, for example, methionine or lysine, can be added. The fats are employed in the form of plant or animal fats or waste fats. For body building, there are added further salts, such as dicalcium phosphate, calcium carbonate, and common salt. Optionally, the feed mix is balanced by the addition of trace elements, vitamins, ballast substances, etc. Also substances produced fermentatively, such as single cell proteins from petroleum fractions or alcohols, various yeasts, algae protein or others, possibly also substances recovered from waste materials, can be a component part of the feed formulation, even to a considerable degree.

The animal feed mixtures of the invention contain, in addition to the usual components adapted for certain animal species or feed use, 5 to 50 ppm, preferably 10 to 40 ppm, of the mentioned antibiotic tylosin, depending on the age of the animal and the type of feed mixture, and the proteolytic enzymes in a quantity such that the enzymatic activity is from 0.05 to 2.5 mTU/gm, preferably 0.2 to 0.5 mTU/gm.

The above-mentioned additive concentrations refer to the content in the total feed mixture. For concentrates or supplemental feeds the concentrations are correspondingly higher. In particular, a combination of tylosin and an acid fungus protease or protease mixture is used. The weight increase or, respectively, the improvement in the feed utilization obtained thereby amounts to as much as 6% in comparison with corresponding control mixtures containing only the antibiotic.

The active combination of tylosin and proteolytic enzymes is especially successful in feed for piglet raising and the fattenings of pigs. However, it can be utilized also for all other kinds of animals where the use of tylosin alone is already of advantage.

The antibiotic is expediently added to the feed in the form of a premix, for example, combined with extracted soybean meal pellets. By using mixed meal type feed compositions, the enzyme component can also be applied as a premix. Here, as carrier substance, any feed component can be used, for example, again extracted soybean meal pellets. When employing steam-tempered pelletizing of animal feeds, the admixture of the enzymes must occur in a suitably stabilized form to prevent deactivation by moisture and heat during the pelletizing. Such a method is the subject, for example, of the U.S. Patent Application Ser. No. 760,358, filed Jan. 19, 1977, now abandoned.

To determine the enzymatic activity of the enzyme unit (TU), the proteolytic activity of the protease is ascertained by the known principle of Anson. A suitably diluted quantity of enzyme solution is incubated for 20 minutes at 40° C. with an equal volume of a 1.2% casein solution, the latter containing 0.6% lactic acid, 6 moles of urea and 0.1 mole of citric or acetic acid. The pH value of the casein solution is adjusted to 4.5 by addition of 2 N sodium hydroxide solution. After the incubation, the procedure is to admix with 0.4 N trichloroacetic acid in the volumetric ratio 1:1. The produced precipitate of undigested casein is filtered, and the protein cleavage products formed during degradation are ascertained in the filtrate by any method of protein determination. Suitable for this is, for example, the method described by Layne in *Method of Enzymology* 3 (1957), pages 448 ff.

For each test sample a blank value must be produced, wherein first trichloroacetic acid and then casein solution is added. This blank value indicates, in addition to the reagent blank value, the proportion of peptides of low molecular weight already present before the digestion in the enzyme solution. The difference between main and blank value is then compared, following the indicated method, with the extinction, which is given by a predetermined amount of tyrosine. This amount of tyrosine is then a measure of the proteolytic activity of the enzyme being determined. One enzyme unit (TU) is that amount of enzyme which releases in one minute from the casein solution the cleavage products which have the same extinction value as 1 M tyrosine solution. It is customary to express this in $mTU = 10^{-3} TU$.

The following examples are illustrative of the invention without being limitative in any respect.

EXAMPLE 1

259 piglets in the weight range from an average 7.24 kg to an average 23.34 kg were fed with an identically composed raising feed, but which (a) was without addition of antibiotic or enzyme,
(b) had an addition of 40 ppm tylosin, or
(c) had an addition of 40 ppm tylosin and 0.45 mTU/gm of acid proteases from Rhizopus rhizopodiformis and Aspergillus niger.

The animals were maintained in flat cages in groups of 7 or 8 animals. Feeding was ad libidum. For acclimatization, all groups were given an identically composed starter feed at an average weight of about 6.92 kg. Thereafter, the animals received the actual test mixtures (see above).

By regular weighing the growth curve and the feed utilization were determined. The "feed utilization" is the ratio of feed consumption to the weight gain.

TABLE 1

| Feed Composition (%) | % by Weight |
|---|---|
| Protein feed consisting of: | 18% |
| 62.5% soybean meal pellets (44% raw protein), | |
| 25% fish meal | |
| 12.5% mineral substance and vitamin premix | |
| Oats | 14% |
| Wheat bran | 10% |
| Barley | 28% |
| Wheat | 15% |
| Corn | 15% |
| | 100% |

| RESULTS | TOTAL DAILY WEIGHT INCREASE (gms) | Feed Utilization |
|---|---|---|
| (a) Without addition | 364.2 | 1.98 |
| (b) with tylosin | 375.3 | 1.99 |
| (c) with tylosin and enzyme | 380.8 | 1.87 |

The preceding Example clearly demonstrates that the presence of both the antibiotic tylosin and proteolytic enzymes, preferably acid proteases, increases both the total daily weight increase and feed utilization ratio.

The preceding specific embodiments are illustrative of the practice of the invention. It is to be understood, however, that other expedients known to those skilled in the art or disclosed herein, may be employed without departing from the spirit of the invention or the scope of the appended claims.

I claim:

1. A high efficiency animal feed for the feeding of piglets and the fattening of pigs comprising carbohydrates, protein and fats and optionally conventional additives, having a content of 10 to 40 ppm of the antibiotic tylosin and a content of acid proteolytic enzymes derived from Aspergillus niger, from the genus Tramates or from Rhizopus rhizopodiformis, having a wide spectrum of action and a range of 50% of maximum activity between a pH of 2.5 and a pH of 6.5 in such an amount that an enzymatic activity of 0.2 to 0.5 mTU/gm of said animal feed is produced.

2. A method for efficient rearing of piglets and the fattening of pigs comprising feeding said piglets or pigs a high efficiency animal feed comprising carbohydrates, proteins and fats and optionally conventional additives, having a content of 10 to 40 ppm of the antibiotic tylosin and a content of acid proteolytic enzymes derived from Aspergillus niger, from the genus Tramates or from Rhizopus rhizopodiformis, having a wide spectrum of action and a range of 50% of maximum activity between a pH of 2.5 and a pH of 6.5 in such an amount that an enzymatic activity of 0.2 to 0.5 mTU/gm of said animal feed is produced.

* * * * *